(12) United States Patent
Edelbrock et al.

(10) Patent No.: US 9,097,659 B2
(45) Date of Patent: Aug. 4, 2015

(54) MAINTAINING ELECTRODE FUNCTION DURING MANUFACTURE WITH A PROTECTIVE LAYER

(71) Applicant: Bayer HealthCare LLC, Tarrytown, NY (US)

(72) Inventors: Andy Edelbrock, Granger, IN (US); Steven C. Charlton, Osceola, IN (US)

(73) Assignee: Bayer HealthCare LLC, Whippany, NJ (US)

( * ) Notice: Subject to any disclaimer, the term of this patent is extended or adjusted under 35 U.S.C. 154(b) by 212 days.

(21) Appl. No.: 13/829,447

(22) Filed: Mar. 14, 2013

(65) Prior Publication Data

US 2014/0262772 A1   Sep. 18, 2014

(51) Int. Cl.
G01N 27/416 (2006.01)
A61B 5/15 (2006.01)
C12Q 1/00 (2006.01)
C23C 28/00 (2006.01)
G01N 27/327 (2006.01)

(52) U.S. Cl.
CPC ............ *G01N 27/416* (2013.01); *A61B 5/15* (2013.01); *C12Q 1/00* (2013.01); *C23C 28/00* (2013.01); *G01N 27/3272* (2013.01); *Y10T 29/49224* (2015.01)

(58) Field of Classification Search
CPC ...... A61B 5/150274; C12Q 1/00; C12Q 1/54; G01N 27/327; G01N 27/3272; G01N 27/416; C23C 28/00
USPC ............ 204/403.01–403.15; 29/885; 156/256
See application file for complete search history.

(56) References Cited

U.S. PATENT DOCUMENTS

| | | | |
|---|---|---|---|
| 6,531,040 B2 | 3/2003 | Musho et al. | |
| 6,656,702 B1* | 12/2003 | Yugawa et al. | 435/26 |
| 7,862,696 B2 | 1/2011 | Wu et al. | |
| 7,966,859 B2 | 6/2011 | Wu et al. | |
| 2002/0053523 A1 | 5/2002 | Liamos et al. | |
| 2002/0120186 A1 | 8/2002 | Keimel | |
| 2006/0037870 A1 | 2/2006 | Deng et al. | |
| 2008/0169206 A1* | 7/2008 | Pei et al. | 205/780.5 |
| 2008/0199937 A1* | 8/2008 | Chu et al. | 435/200 |
| 2008/0248581 A1* | 10/2008 | Chu et al. | 436/66 |
| 2009/0145756 A1* | 6/2009 | Zhu et al. | 204/403.14 |
| 2009/0152111 A1* | 6/2009 | Miyazaki et al. | 204/403.14 |
| 2009/0159197 A1* | 6/2009 | Edelbrock | 156/280 |

(Continued)

FOREIGN PATENT DOCUMENTS

WO    0113103 A1    2/2001
WO    0202796 A2    1/2002

(Continued)

OTHER PUBLICATIONS

International Search Report and Written Opinion for Application No. PCT/US2014/021845 dated Jul. 11, 2014.

*Primary Examiner* — Jennifer Dieterle
(74) *Attorney, Agent, or Firm* — Lerner, David, Littenberg, Krumholz & Mentlik, LLP

(57) ABSTRACT

The present disclosure relates to an electrochemical test sensor for detecting the concentration of an analyte in a fluid sample. The test sensor includes a working electrode, a counter electrode, and a trigger electrode. A temporary protective layer overlies the trigger electrode and helps to maintain the function of the trigger electrode during test sensor manufacture.

25 Claims, 7 Drawing Sheets

(56) References Cited

U.S. PATENT DOCUMENTS

2009/0255811 A1* 10/2009 Forrow et al. ............ 204/403.14
2009/0311598 A1    12/2009 Tadano
2010/0227080 A1*  9/2010 Beer et al. ..................... 427/555
2011/0137143 A1*  6/2011 Fukuda et al. ................ 600/347

FOREIGN PATENT DOCUMENTS

| WO | 2006027703 A2 | 3/2006 |
| WO | 2008100118 A1 | 8/2008 |

* cited by examiner ured for a variety of reasons. First,
MAINTAINING ELECTRODE FUNCTION DURING MANUFACTURE WITH A PROTECTIVE LAYER The present disclosure generally relates to the structure and manufacture of test strips or sensors and, more particularly, to improved sensors with protective coatings for trigger electrodes.

BACKGROUND OF THE INVENTION

Monitoring systems are used for determining the presence or concentration of analytes in body fluids, such as glucose, cholesterol, alcohol, and hemoglobin in blood, interstitial fluid, or chemical substances in saliva. These monitoring systems require frequent use of test sensors, which are commonly used to test harvested blood or any other suitable liquid sample.

Typically, a user will deposit a test sample of the biological liquid on a sample receiving area or pad either in fluid communication with the test sensor, or forming a portion of the test sensor. The biological liquid sample is permitted to wick along the test sensor to a predefined testing area that includes a reagent capable of a readable change when contacted by a predetermined constituent in the test sample.

Test sensors commonly include at least a pair of electrodes, including a working electrode and a counter electrode. Test sensors also commonly include a third electrode, a trigger electrode. The trigger electrode is electrically in parallel with the counter electrode but, when clean, can supply a small current pulse, which can be used to start the meter timing sequence and detect whether the sensor is inadequately filled with fluid sample.

The test sensor also includes a dry reagent in contact with the working electrode and counter electrode, and a capillary flow channel extending from an inlet opening to the working and counter electrodes. The reagents typically include an enzyme that is capable of oxidizing the glucose in the sample, such as glucose oxidase and one or more mediators adapted to reoxidize the reduced enzyme resulting from oxidation of the glucose, thereby forming a reduced mediator. The test sensor is inserted into a meter so that the working and counter electrodes are electrically connected to the components within the meter. After the test sensor is inserted in the meter, a sample of a bodily fluid, such as blood, is introduced into the capillary flow channel and contacts the trigger electrode, if present, working electrode, counter electrode and reagent, whereupon the components within the meter apply one or more electrical voltages between the working and counter electrodes. These electrodes transmit the electrical signals generated by the test sensor to a processor in the meter and the electrical current passing between the electrodes is measured. The reduced mediator is oxidized at the working electrode, thereby producing a measurable current which is related to the amount of reduced mediator present at the working electrode, and therefore related to the concentration of glucose in the fluid. The measured current typically begins at a high value and then declines and approaches a constant value. For example, the current measured at a predetermined time during application of a voltage may be used to determine the glucose content of the sample. The processor then analyzes these signals and displays the results (e.g., analyte concentration level) to the user via a display device.

Accurate test results are dependent on a variety of factors, including providing an appropriate amount of fluid sample on the test sensors and properly functioning electrodes. To help provide more accurate test results, test sensors commonly include a third electrode, sometimes referred to as a trigger electrode. The trigger electrode is electrically in parallel with the counter electrode, but is capable of supplying a small current pulse. This pulse can be used to start the meter timing sequence to begin testing at a point in time in which the sensor is adequately filled with fluid sample. Similarly, the pulse can be used to determine whether there is an inadequate amount of fluid sample on the sensor and testing should not begin. The trigger electrode can therefore serve as an indicator as to when it is appropriate for testing of the fluid sample to begin.

Trigger electrodes are commonly positioned upstream of both the working and counter electrode toward an outermost edge of the test sensor. Because of its position at the edge of the test sensor, trigger electrodes are often contaminated by smoke and other byproducts created during manufacture of the test sensor. During test sensor manufacture, the final shape of the test sensor must be cut out from a laminated multilayer structure. Laser cutting is one method of cutting out the test sensor that provides accurate and reliable results. However, as the front edges of the test sensor are cut out, smoke from the laser contaminates the trigger electrode. In addition, the use of catalytic noble metals, such as gold, platinum, and palladium, can result in the adsorption of airborne contaminants that can also foul the surface and make it less reactive and able to function as a trigger electrode.

Contaminants on the trigger electrode are one common cause of trigger electrode malfunction and inaccurate test results. When the trigger electrode does not function properly, the test may fail to start at the appropriate time. Conversely, the trigger electrode may fail to indicate that there is an insufficient amount of fluid sample on the test sensor and testing should be delayed.

In view of the shortcoming associated with contaminated trigger electrodes, it is desirable to provide a test sensor and a method of making a test sensor that can minimize contamination of the trigger electrode during test sensor manufacture.

BRIEF SUMMARY OF THE INVENTION

In accordance with one aspect of the present invention, an electrochemical test sensor for detecting the concentration of an analyte in a fluid sample includes a base, a plurality of electrodes, including a trigger electrode, a protective layer overlying the trigger electrode, and a lid. The base may be a non-conductive base that has a top surface, a bottom surface, and a peripheral edge extending between the top and bottom surfaces. The electrodes may additionally include a working electrode and a counter electrode. All of the electrodes will overlie the non-conductive base. The trigger electrode may be positioned adjacent the peripheral edge of the base. The protective layer may overlie at least a portion of the trigger electrode and is preferably soluble upon contact with the fluid sample. An insoluble layer can be used as long as performance of trigger electrode function remains acceptable after contamination. A reactive layer may be provided on at least a surface of the working electrode. The reactive layer may include an enzyme for reacting with the analyte to produce electrons which are transferred to the working electrode. The lid overlies the base and has a top surface, a bottom surface, and an outer edge extending between the top and bottom surfaces. The outer edge of the lid extends beyond the peripheral edge of the base.

In one embodiment of this aspect of the test sensor, the protective layer is comprised of a polymer solution, such as carboxymethyl cellulose. The polymer solution may have a concentration ranging between 0.25% and 1.0%. For example, the polymer solution may have a concentration of 0.25%. Alternatively, the polymer solution may have a concentration of 1.0%. The protective layer may also be formed from other solutions. Surfactant or rheological additives may be included for improved application. Visualizing agents may also be added for inspection of drop placement and/or thickness.

In accordance with another embodiment of this aspect, a conductive layer overlies the base. In one embodiment, the base is laminated, coated or sputtered with the conductive layer. The conductive layer may be a metallic layer or a carbon layer. Each of the working, trigger, and counter electrodes may by patterned from the conductive layer. In accordance with another embodiment, the test sensor further comprises a spacer overlying the base. The spacer may be positioned between the reactive layer and the lid and have a channel that extends through the spacer. The channel may be aligned with the working and trigger electrodes.

In accordance with another aspect, a method of manufacturing an electrochemical test sensor for detecting the concentration of an analyte in a fluid sample is disclosed. The method includes patterning a plurality of electrodes from a conductive layer overlying a base, including a trigger electrode, a working electrode, and a counter electrode. A reactive layer overlies the working electrode and counter electrode. A protective layer overlies the trigger electrode and a reactive layer is deposited so as to overlie the working electrode. A spacer is positioned between the base and a lid. A first opening is created that extends through the spacer and the base. A second opening is created in the lid so that the first opening and the second opening are created in two separate steps. A test sensor is then excised.

In accordance with another embodiment, the first opening has an inner peripheral edge and the second opening has an inner peripheral edge, of which at least a portion of the inner peripheral edge of the second opening extends beyond the inner peripheral edge of the second opening so as to create an overhang.

In accordance with another embodiment, the step of providing a protective layer includes providing a polymer layer. The step of applying a polymer layer may comprise applying a layer of carboxymethyl cellulose or hydroxyethyl cellulose.

In accordance with another embodiment, the step of patterning comprises ablating through at least a portion of the metallic layer with a laser so as to form an electrode pattern. The metallic layer may be provided on a flexible insulating substrate.

In accordance with another embodiment, a layer of gold overlies the base. The step of patterning the metallic layer may include patterning the gold layer.

In accordance with still another embodiment, the step of providing the lid occurs after the step of providing an opening through the base and spacer. Alternatively, the step of providing an opening further comprises laser cutting an opening.

In accordance with another embodiment, the lid is constructed and arranged so the openings are aligned, but the edges of the lid extend beyond the edge of the trigger electrode.

In accordance with another embodiment, the step of providing a protective layer may also include a surfactant or rheological additive for increased wettability or processability.

BRIEF DESCRIPTION OF THE DRAWINGS

Various embodiments will now be described with reference to the appended drawings. It is to be appreciated that these drawings depict only some embodiments of the invention and are therefore not to be considered limiting in their scope.

DETAILED DESCRIPTION

It will be appreciated that various features set forth in the embodiments discussed herein can be combined in different ways than presented herein. It will also be appreciated that the features described in connection with individual embodiments may be shared with other embodiments discussed herein.

Figure 1:
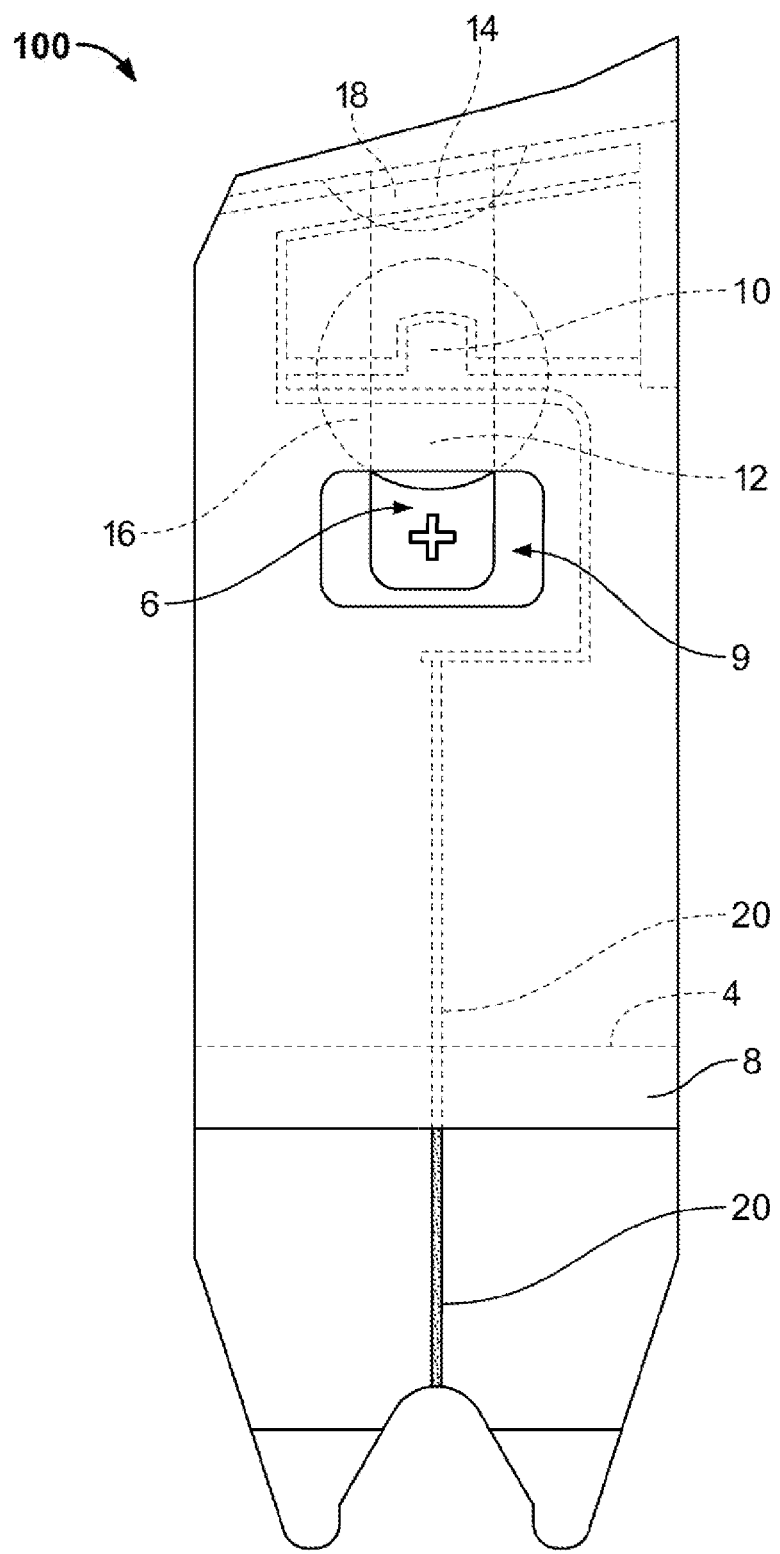
FIG. 1 is a top-plan view of a test sensor in accordance with one embodiment.
Figure 2:
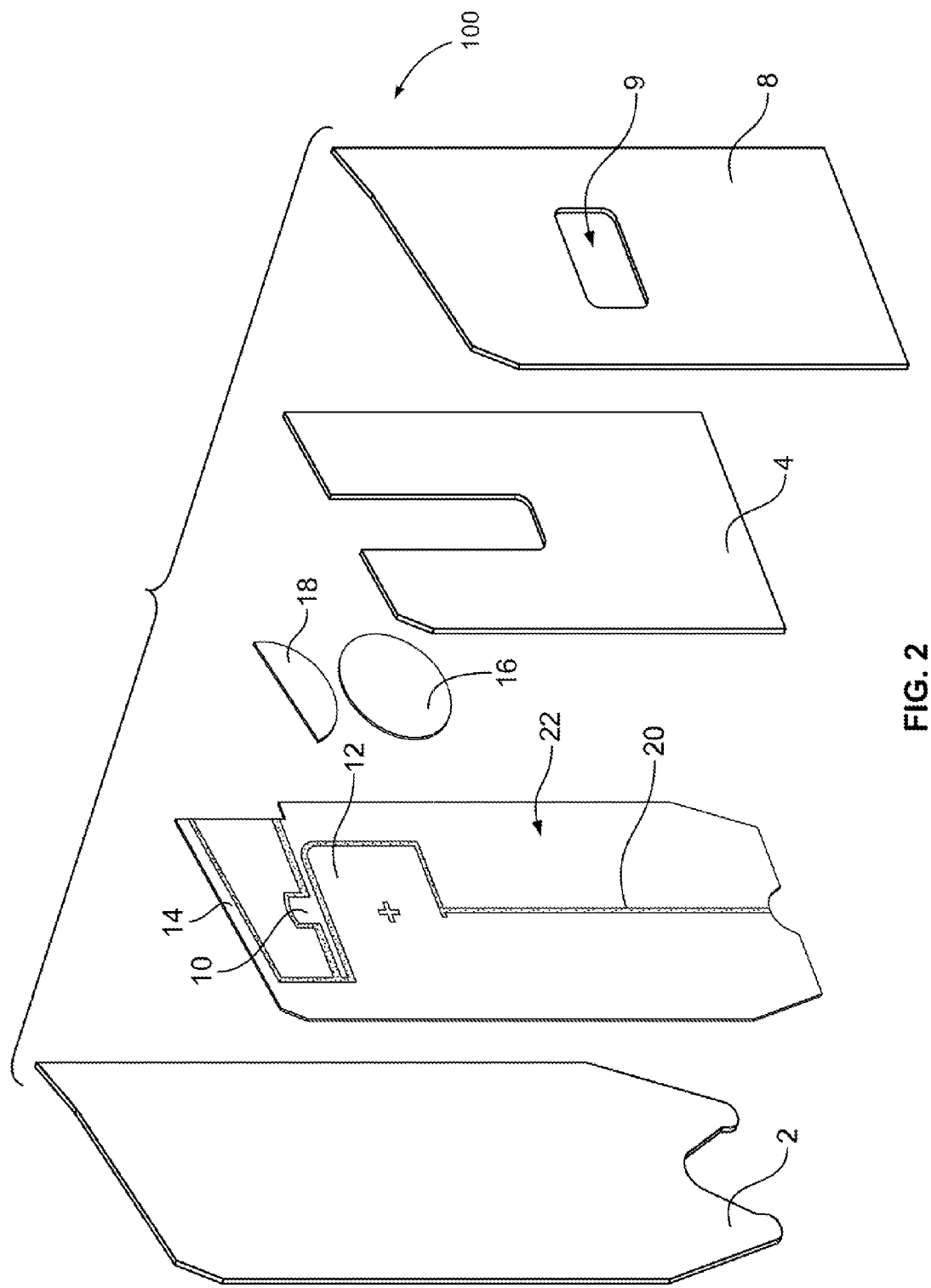
FIG. 2 is a perspective exploded view of the test sensor shown in FIG. 1.

Turning to FIGS. 1 and 2, a respective top-plan view and exploded top-plan view of a test sensor 100, there is shown an electrochemical and multilayer biosensor or test sensor 100 in accordance with one embodiment. The test sensor 100 includes a base 2, spacer 4, capillary channel 6, lid 8, and a plurality of electrodes (working electrode 10, counter electrode 12, and trigger electrode 14), which may be formed or printed on base 2. Reactive layer 16 overlies base 2 and working electrode 10 and may also overlie the counter electrode 12. Protective layer 18 overlies base 2 and trigger electrode 14. A plurality of conductive leads 20 or traces of the respective electrodes extend across test sensor 100.

As best seen in FIG. 2, base 2 forms the foundation for test sensor 100. Base 2 may be comprised of an insulative material, such as a polymeric material. Examples of polymeric material may include polycarbonate, polyethylene terephthalate (PET), polystyrene, polyimide, and combinations thereof. A layer of conductive material 22 may be deposited onto a surface of base 2 using known methods such as, for example, sputtering, coating or printing. The conductive material 5 may include metallic materials (e.g., gold, platinum, palladium, rhodium, ruthenium, or combinations thereof) or carbon. Desired electrodes may be screenprinted, patterned, ablated, etched, scribed or formed from the conductive material on base 2, including working electrode, counter electrode, and trigger electrode, all of which are conventional electrodes known in the art. Lasers or known methods to form each of the electrodes may be used. When the working electrode, counter electrode, and trigger electrode are electrically connected through a meter, an electrochemical current or potential is created among them. Capillary channel 6 is formed when spacer 4, base 2, and lid 8 are attached to one another. Capillary channel 6 provides an enclosed flow path for introducing the fluid sample into the test sensor 100 and eventually contacting each of electrodes 10, 12, 14. Lid 8 also provides an opening 9, which provides a vent structure for the test sensor 100.

Working electrode 10 and counter electrode 12 are necessary for the electrochemical determination of the analyte in a fluid sample. Working and counter electrodes 10, 12 are configured in a manner such that the major portion of the counter electrode 12 is located downstream (in terms of the direction of fluid flow along the flow path) from the forward position of the working electrode 10.

Reactive layer 16 overlies working electrode 10. Reactive layer 16 includes a reagent for converting an analyte of interest (e.g., glucose) in a fluid test sample (e.g., blood) into a chemical species that is electrochemically measurable, in terms of the electrical current it produces, by the components of the electrode pattern. The reagent typically contains an enzyme (e.g., glucose oxidase), which reacts with an analyte (e.g., glucose) and with an electron acceptor (e.g., a ferricyanide salt) to produce an electrochemically measurable species that can be detected by the electrodes. For example, the enzyme which reacts with the analyte can produce electrons that are transferred to the working electrode 10. The reactive layer 16 may comprise a polymer, an enzyme, and an electron acceptor. Additional ingredients such as a buffer and a surfactant may also be included in the reactive layer 16 in other embodiments. It is contemplated that alternative known enzymes may be used to react with glucose, such as glucose dehydrogenase. If the concentration of another analyte is to be determined, an appropriate enzyme can be selected to react with the analyte.

Trigger electrode 14 is electrically parallel to counter electrode 12. Trigger electrode 14 carries no reagent, but is capable of supplying a small current pulse that can be used for starting the meter timing sequence or for detecting an inadequately filled sensor. For example, to provide an accurate test result, a sufficient amount of fluid sample must be provided to cover all of the electrodes (i.e., the trigger electrode 14, working electrode 10, and counter electrode 12). When there is an insufficient amount of fluid sample, such as when the fluid sample (e.g., blood) covers only two of the three electrodes (e.g., only the trigger electrode 14 and the working electrode 10), trigger electrode 14 may provide a negative current or a pre-determined value of current to inform the system that there is an inadequate amount of fluid sample on the test sensor 100. Examples of the various features of trigger electrode 14 are well known in the art. One example of a functioning electrode used to determine whether there is an inadequate amount of fluid sample in the test sensor or the test sensor is underfilled is disclosed in U.S. Pat. No. 7,966,859, the disclosure of which is incorporated herein by reference. Similarly, when there is a sufficient amount of fluid sample on test sensor 100, trigger electrode 14 may provide a different current signifying the start of the testing procedure.

A protective layer 18 directly overlies trigger electrode 14 and covers the entire top surface of trigger electrode 14. Protective layer 18 may be a film overlying trigger electrode 14 that functions to protect trigger electrode 14 during the test sensor manufacturing process. In one embodiment, protective layer 18 protects trigger electrode 14 from smoke that emanates during laser cutting of the final shape of the test sensor. In other embodiments, protective layer 18 may protect trigger electrode 14 from abrasion and adsorption of impurities in the air that can cause fouling of the trigger's reactive surface.

Composition of the protective layer 18 is chosen to be protective of the electrodes but not detrimental to analytical performance or stability of the chemistry. It can be comprised of a polymer solution, such as carboxymethyl cellulose (CMC) or hydroxyethyl cellulose (HEC) at concentrations of 0.25% or 1.0%. Surfactant or rheology modifying additives may be included to improve deposition. Visualizing agents may also be added for inspection of drop placement and/or thickness. An insoluble protective layer may be used as long as performance of trigger electrode function remains acceptable after contamination. In this context, an insoluble protective layer is one that remains essentially intact during the assay time of about 10 seconds. Examples of such layers are high molecular weight substituted cellulose or ethylene oxide polymers. Protective layer 18 may be deposited directly onto the trigger electrode 14 in an amount sufficient to cover, at a minimum, 5% of the trigger area in relation to the working electrode size, but ideally will cover a majority of trigger electrode 14. While the amount of selected solution should be sufficient to cover at least a majority of the electrode, it should not mix or make contact with the reactive layer 16 that is deposited on the working and counter electrodes 10, 12. In one embodiment, protective layer 18 is a droplet of polymer solution sufficient in size and placement to cover a minimum of at least 5% of the available trigger area in relation to the working area and up to a drop which covers trigger electrode 14 in its entirety, but makes no contact with reactive layer 16. Larger drops placed further away or smaller drops placed closer to the trigger electrode may be used to achieve the same end. Fulfillment of electrode size and placement requirements may be monitored by inspection such as a camera system. Drop thickness may also be monitored by a camera system or by analyzing protective components after extraction.

In alternative embodiments, one or more small drops may be deposited that provide coverage of the trigger electrode while reducing the possibility of the drops making contact with the reactive layer. Alternatively, surface features that have been patterned or ablated in the conductive coating of the base and/or properties of the base may be used to shape or steer the drop. In still other embodiments, a test sensor coating method may be used to provide coverage on the trigger electrode.

In accordance with one embodiment, the protective layer 18 is a thin layer. Allowing the protective layer 18 to become too thick prevents protective layer 18 from rehydrating fast enough. This causes the test sensor to be slow to start in an underfill condition. For example, although not limited to such measurements, protective layer 18 may be as thin as 1-10 um. In some embodiments, HEC and CMC are selected at concentrations of 1% and below. When the percent polymer goes above 1%, rehydration can be too slow.

Protective layer 18 serves to protect the trigger electrode from contamination not only during manufacture, but also during handling of the test sensor, as the user grasps and then inserts the test sensor into the meter. One feature of protective layer 18 is that performance of trigger electrode function remains acceptable even after contamination. This allows for the trigger electrode to be covered or protected during manufacture and handling of the test sensor by the protective layer, but fully functional during the actual testing process. In one embodiment, protective layer 18 is rapidly dissolvable. The fluid sample itself can rapidly dissolve the protective layer 18 to gain access to the electrodes. The polymer solutions discussed herein were selected for their ability to readily dissolve upon contact with fluid sample, but other solutions that are capable of dissolving may also be used. Analytical accuracy is not compromised by dissolved or leached components of the protective layer and any contaminants.

Sensors built with and without the protective coating were tested for functionality, as described below. When the trigger electrode is contaminated, its reactivity or ability to undergo electrochemical reactions is reduced. Reactivity was measured during testing by applying a test solution, a mixture of 200 mM potassium ferricyanide and 5 mM potassium ferrocyanide, to a test sensor in such a way that only trigger electrode and working electrode were functional. The working electrode is not affected by contamination, hence the reactivity measured is only that of the trigger electrode. Currents flowing at applied potentials of 100 mV and 400 mV were measured and used to calculate the activity ratio (i.e., current at 400 mV/current at 100 mV). The current that flows depends on the reactivity of the electrodes and on the applied potential. At low 100 mv potential, the current flowing through a contaminated electrode (one that was laser cut) will be much lower than one flowing through a clean electrode. The activity ratio is therefore indicative of electrode contamination. A functional test is for the timing sequence to start appropriately when the fluid sample passes over the trigger electrode. A test sensor that does not start ("failure to start") is indicative of a contaminated trigger electrode surface. Table 1 below summarizes the results of testing on test sensors at different conditions. Thirty test sensors were tested using the conditions identified on the chart. As shown, Entry 1 is a control test sensor, with no potential contamination from laser cutting and a low (satisfactory) activity ratio. Entry 2 includes a test sensor with a trigger electrode that has been contaminated by smoke from a nearby laser cut, and no post-cleaning of the trigger electrode was performed. The activity ratio is very high and most test sensors (73%) failed to start. Entry 3 shows smoke-contaminated sensors from a nearby laser cut where the electrode has been partially cleaned by reactive gas plasma treatment. Although the activity ratio is improved (i.e., 5.2), it is still unsatisfactory. Moreover, gas plasma treatment is an undesirable extra treatment step that provides added cost.

TABLE 1

| Entry number | Cut (n = 30 samples) | Cleaned post cut | Polymer type | | Measured activity ratio | Failure to start (%) |
| --- | --- | --- | --- | --- | --- | --- |
| | | | Type | Concentration (%) | | |
| 1 | None (control) | No | NA | 0 | 1.9 | 0 |
| 2 | Laser cut | No | NA | 0 | 10 | 73 |
| 3 | Laser cut | Yes | NA | 0 | 5.2 | 0 |
| 4 | Laser cut | No | CMC | 0.5 | 1.7 | 0 |
| 5 | Laser cut | No | CMC | 1.0 | 1.7 | 0 |
| 6 | Laser cut | No | HEC | 0.5 | 2.4 | 0 |
| 7 | Laser cut | No | HEC | 1.0 | 2.5 | 0 |

Entries 4-5 provide the results of a test sensor with CMC deposited on the trigger electrode at concentrations of 0.5% and 1.0%, respectively. As shown by the measured activity ratio, both concentrations of CMC provided protection of the trigger electrode from smoke emanating from laser cuts along the electrode. Moreover, in each set of the 30 test sensors tested at Entries 4-5, each of the 30 test sensors had a 0% failure to start, making use of CMC on the trigger electrode a viable protective layer. Similarly, Entries 6-7 provide the results of a test sensor with HEC deposited on the trigger electrode at concentrations of 0.5% and 1.0%, respectively. Both HEC concentrations provided protection of the trigger electrode, the measured activity ratio being 2.4 and 2.5, respectively. Additionally, test sensors at both HEC concentrations had a 0% failure to start. It is to be noted that while all test sensors in the study started appropriately, the reactivity ratio for test sensors with CMC and HEC were the only ones in this situation that would be considered robust in a manufacturing environment.

Other electrodes may also be incorporated into the test sensor. In just one example, it may be desired to include a hematocrit electrode. Thus, it is contemplated that a greater number of electrodes can be formed in accordance with alternative test sensors and methods of making the test sensor. For example, in the embodiment disclosed herein, the test sensor may include exactly two electrodes with a trigger electrode portion. Alternatively, there may be more than two electrodes. For example, there may be at least three electrodes or four electrodes, depending on the additional electrodes desired to be incorporated into the test sensor 100.

Figure 3:
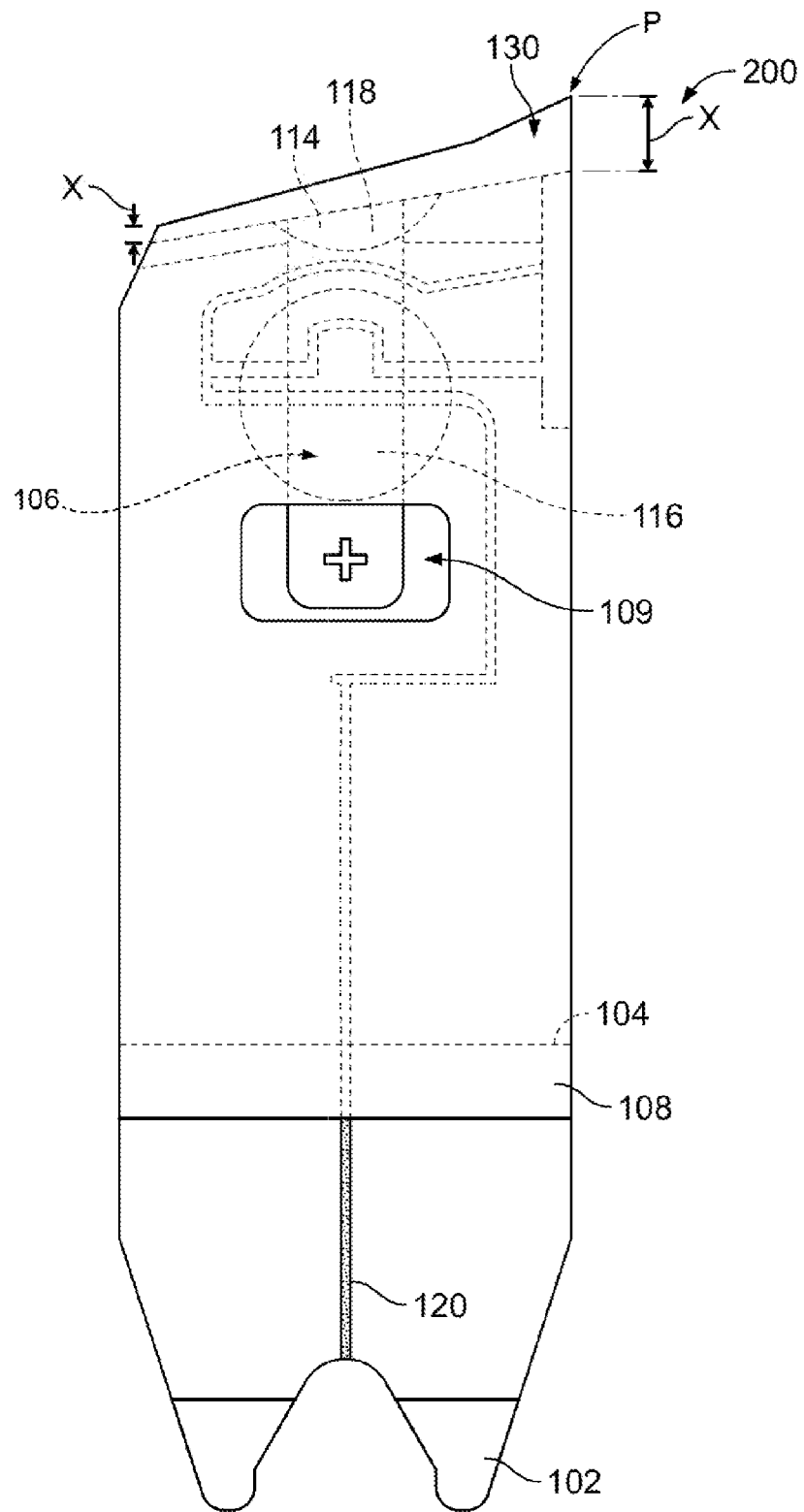
FIG. 3 is a top-plan view of a test sensor in accordance with an alternative embodiment.
Figure 3A:
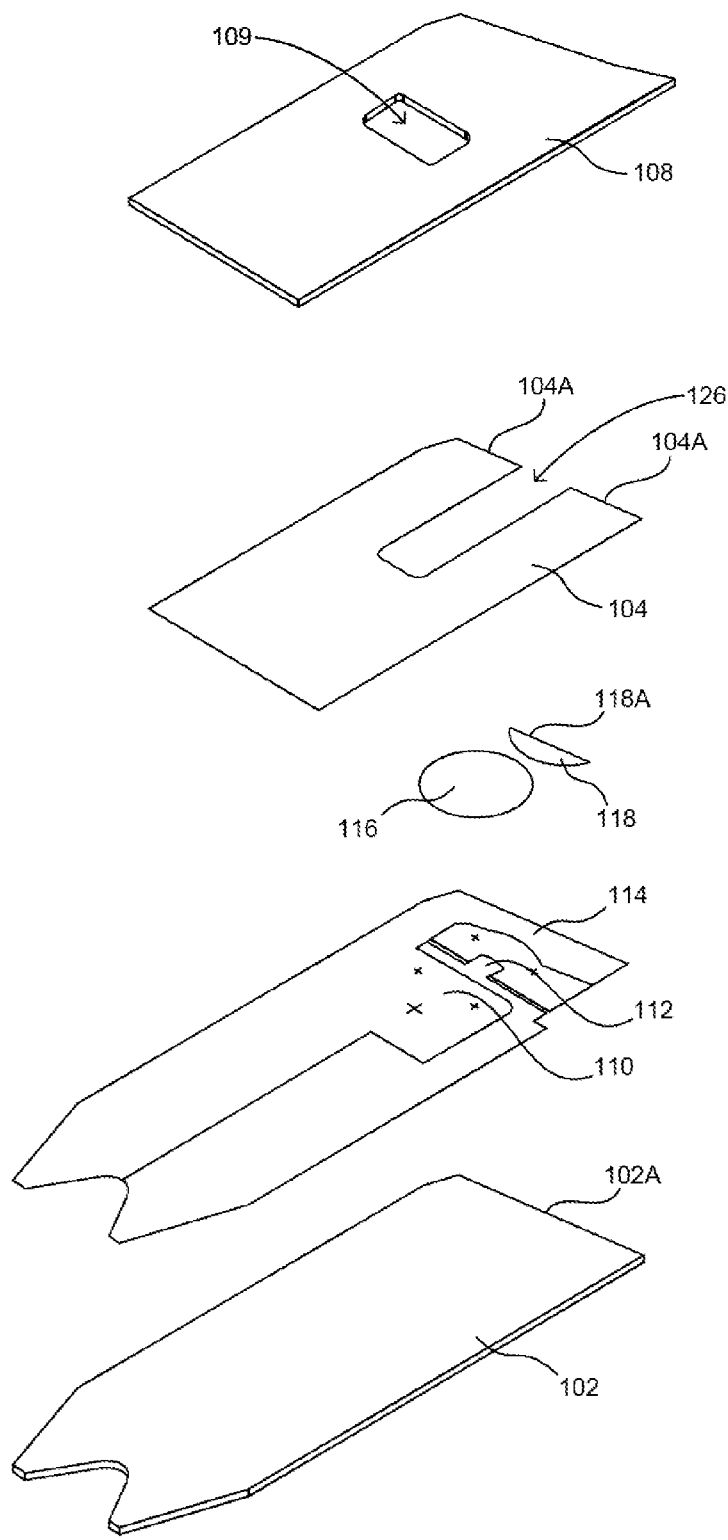
FIG. 3A is an exploded view of the test sensor shown in FIG. 3.

Turning now to FIGS. 3-3A, an alternative embodiment of a test sensor 200 is shown. In this embodiment, similar reference numerals will be used to describe like elements. Test sensor 200 is similar to test sensor 100, differing only to the extent that trigger electrode 114 of FIG. 3 has not been patterned from the conductive layer and does not have a predefined shape. Trigger electrode 114 of test sensor 200 can be defined by the shape of the test sensor 200 excised from the base 102-lid 108 laminate (FIG. 4H) after the spacer 104 has been attached or laminated to base 102. Moreover, spacer channel 126 of spacer 104 will determine the final size and shape of trigger electrode 114. Delaying formation of the overall shape of trigger electrode 114 until final formation of test sensor 200 provides a way to maximize the final area of trigger electrode 114.

Figure 4C:
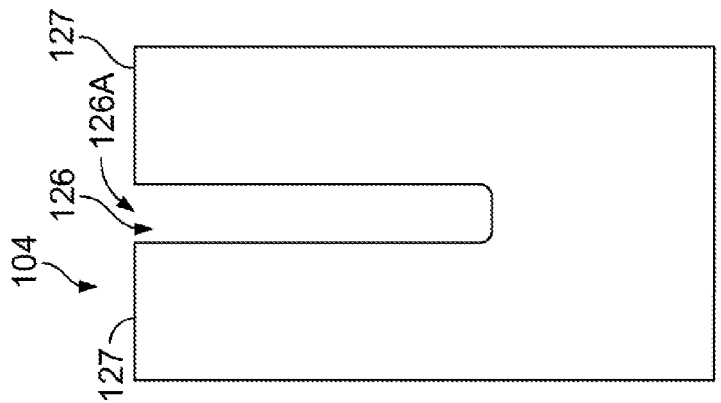
FIGS. 4A, 4B, 4C, 4D, 4E, 4F, 4G, and 4H are top-plan views illustrating method steps in the manufacture of the test sensor shown in FIG. 3.
Figure 4B:
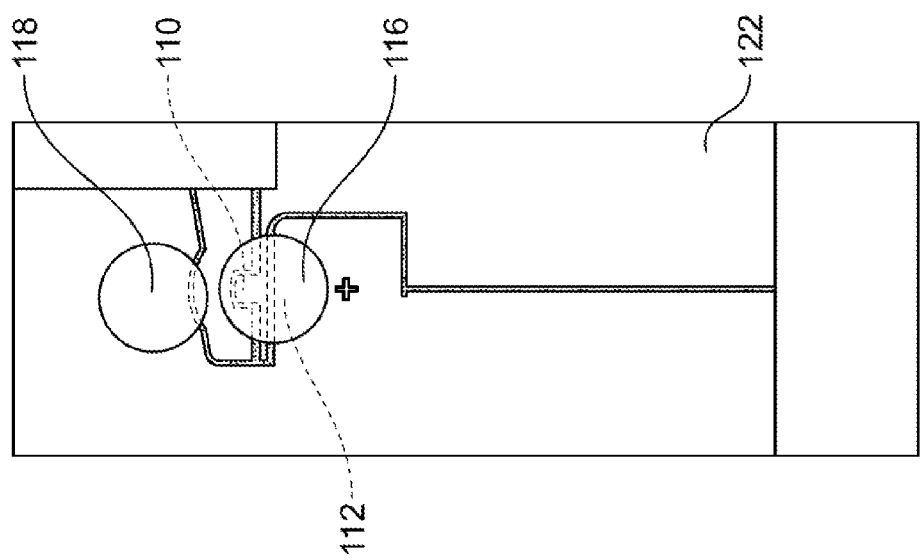
Figure 4A:
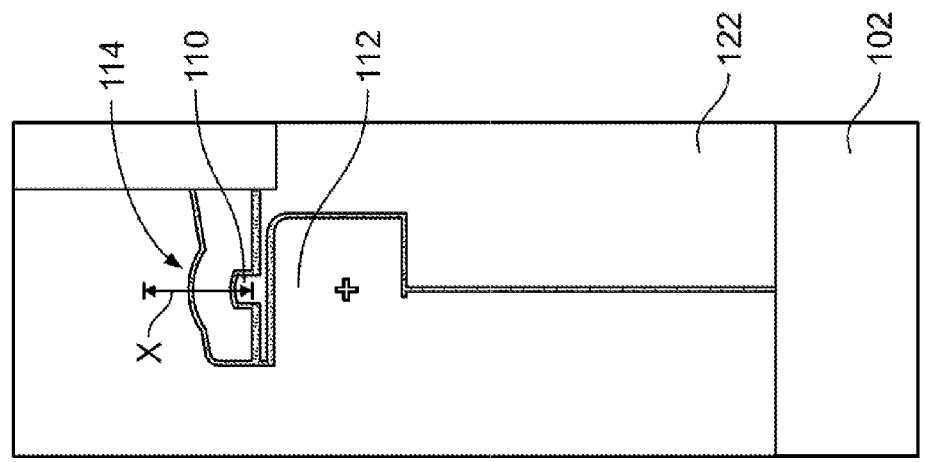

Referring now to FIGS. 4A-4H, a method of manufacturing the test sensor 200 of FIG. 3 is shown. As shown in FIG. 4A, a conductive layer 122 such as, for example, a layer of metallic materials (e.g., gold, platinum, palladium, iridium, rhodium, ruthenium, or combinations thereof) or carbon is provided on base 102 with a conductive layer 122 provided thereon. The conductive layer 122 may be ablated, so as to form electrode patterns thereon. In the example shown, counter electrode 112, and working electrode 110 are patterned from conductive layer 122. To accommodate the presence of protective layer 118 (FIG. 4B), working electrode 110 and the general area providing the final position of trigger electrode 114 may be positioned further away from one another than typical spacing between a trigger electrode and working electrode. The distance X (FIG. 4A) between the trigger electrode 114 and working electrode 110 only needs to be increased to the tolerance capability of the reagent and protective coating placement. With reference to FIG. 4B, since methods used to apply either reactive layer 116 or protective layer 118 may vary, the anticipated increased distance will vary. Drop placement techniques typically are in the 0.05 mm capability, and therefore the additional tolerance in this scenario would be an additional 0.05 mm. This additional spacing also allows for the reactive layer 116 and protective layer 118 to be deposited onto the electrodes without interference between reactive layer 116 and protective layer 118. As shown, protective layer 118 is deposited directly over trigger electrode 114, whereas reactive layer 116 is deposited over the working electrode 110 and counter electrode 112.

Protective layer 118 may be deposited onto trigger electrode 114 using known techniques, such as dropping; deposition of a single drop from a nozzle not in contact with the base; deposition of a single drop from a tube that is in contact with the base; a printing method, such as screen printing; or a continuous stream, provided the deposition device is in movement relative to the test sensor. In the example shown, protective layer 118 is shown as a circular area covering the trigger electrode 114 and the immediately surrounding areas. Protective layer 118 does not extend across the entire surface of conductive layer 122. Furthermore, protective layer 118 is spaced a sufficient distance away from reactive layer 116 so as not to overlap or contact reactive layer 116. It is to be appreciated that protective layer 118 can take on additional shapes or sizes provided that protective layer 118 does not overlap or contact reactive layer 116 and covers at least a portion of the trigger electrode. As previously discussed, it is important that protective layer 118 does not compromise the analytical performance of the reagent. Protective layer 118 should be in the form of a thin coating overlying trigger electrode 114.

Reactive layer 116 may be deposited on the conductive layer 122 using known techniques, such as the techniques disclosed for the protective layer, printing, liquid deposition, or ink-jet deposition. When thinner reagent layers are preferred, deposition methods other than printing, such as micropipetting, ink jetting, or pin-deposition, may be required. Methods of depositing the reactive layer are disclosed in U.S. Pat. No. 7,862,696, the disclosure of which is incorporated herein by reference. As shown, reactive layer 116 may be circular in shape and covers working electrode 10 and counter electrode 112. Reactive layer 116 does not come into contact with protective layer 118.

Figure 4F:
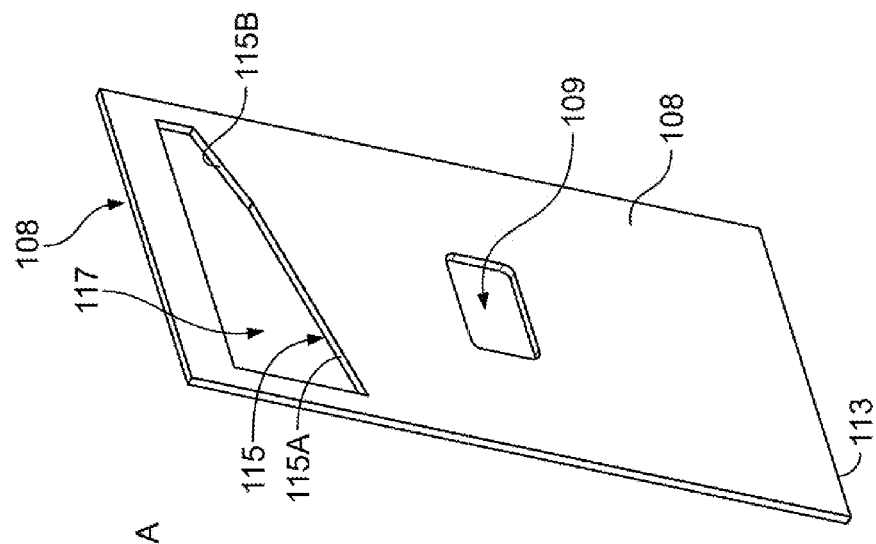

Turning to FIG. 4C, spacer 104 is shown. Spacer 104 may be formed from the same material as base 102 and may be separately manufactured to include a spacer channel 126 extending through a portion of spacer 104. As shown in FIG. 4D, spacer 104 is laminated onto the conductive layer 122, reactive layer 116, and protective layer 118, all of which overlie base 102. Spacer channel 126 is positioned on a portion of spacer 104 so that it will directly overlie electrodes 110, 112, 114. In this embodiment, spacer channel 126 extends along the central portion of spacer 104, such that channel 126 is positioned between the outer edges of spacer 104. Spacer channel 126 has an open end 126A positioned adjacent the top edge 127 of spacer 104. In this embodiment, spacer 104 does not extend across the entire length of base 102, but leaves exposed a portion Y (FIG. 4D) with conductive layer 122 deposited thereon. Meter contacts will touch this exposed conductive layer 122 and provide a path for the current to be measured.

Figure 4E:
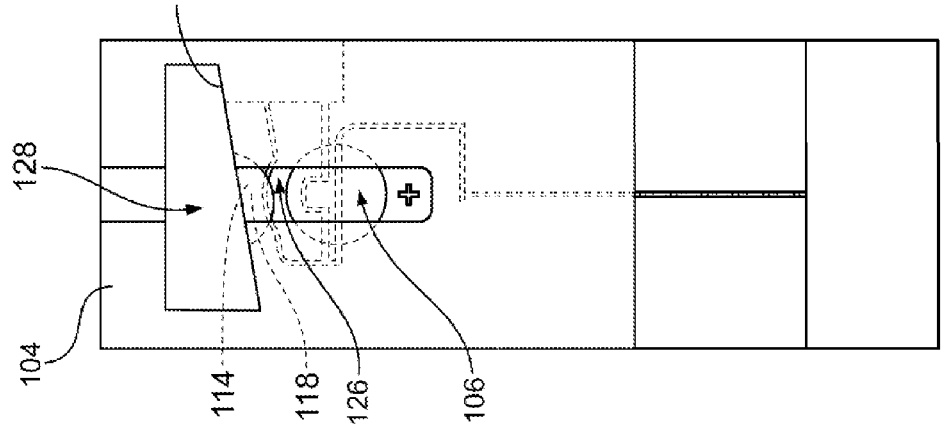
Figure 4D:
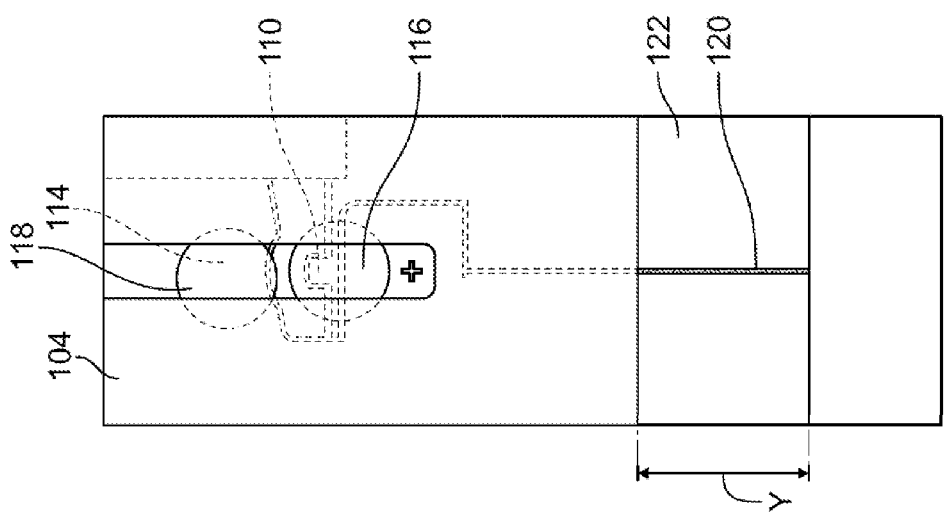

Turning now to FIG. 4E, an opening 128 is made through the base 102, spacer 104 laminate. In this embodiment, opening 128 is laser cut and extends through spacer 104 (including channel 126), protective layer 118, trigger electrode 114, and base 102. Suitable alternative methods may also be used to form the opening, such as mechanical punching or cutting. As shown, trigger electrode 114 is now defined by the area that remains after opening 128 is cut and the area defined by spacer channel 126 (which also helps to define capillary channel 106). Peripheral edge 128A of opening 128 is formed through base 102, spacer 104 laminate. In the process of forming opening 128, a portion of protective layer 118 is cut away to expose an edge 118A (FIG. 3A) of protective layer 118, edge 102A of base 102, and edge 104A of spacer 104. Edges 118A, 102A, 104A are aligned with the first edge 128A of opening 128. (FIG. 2) Peripheral edge 128A of opening 128 is now directly adjacent trigger electrode 114.

During the process of laser cutting, smoke may emanate from the perimeter of opening 128. In this embodiment, protective layer 118 protects trigger electrode 114 from being contaminated by smoke and other contaminants that may result from the laser cutting process. In the absence of protective layer 118, such contaminants can cause trigger electrode 114 to improperly function. For example, trigger electrode 114 may fail to indicate that the system is underfilled and testing should not begin. Similarly, trigger electrode 114 may fail to indicate when testing should begin or may provide a delayed signal as to when testing may begin.

Figure 4G:
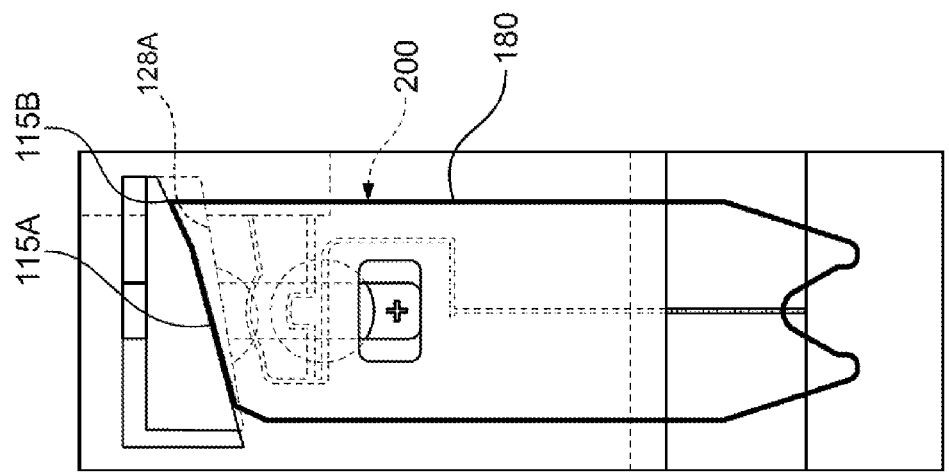

Turning to FIG. 4F, a lid 108 is provided. As shown, lid 108 is precut with a first opening 117 that is precut. Opening 117 has a first edge 115 with a first edge portion 115A and second edge portion 115B. Lid 108 also includes a separate opening 109. Opening 117 is designed so that it overlies channel 126 and first edge 115 extends beyond the edge of trigger electrode 114 and edge 102A of base 102. Turning to FIG. 4G, an overhang portion 130 is created by the portion of lid 108 that extends beyond the edge 102A, 104A of base 102-spacer 104 laminate. Overhang portion 130 (FIG. 3) has a height X that can vary from one edge of test sensor 200 to opposed edge so as to create a sharp point. The features of the overhang can improve the overall design of the test sensor. Lid 108 may have a coating to promote rapid fill of the fluid sample into capillary channel 106. Overhang portion 130 can help to ensure that the fluid sample deposited onto the test sensor 200 makes contact with lid 108 and is then rapidly drawn into capillary channel 106. Moreover, users often hold a test sensor too firmly against their skin, effectively closing off the front of the test sensor and leading to slow fill and degraded performance. Overhang portion 130 makes the sensor resistant to being closed off in this way by spacing the opening of the capillary channel 106 away from the skin.

Figure 4H:
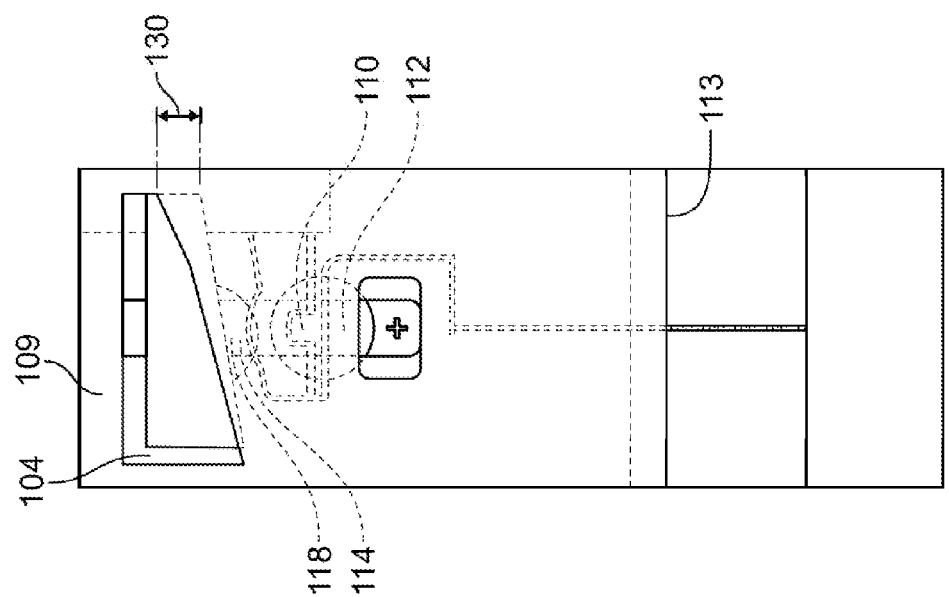

Any desired shape for a test sensor can be obtained. With reference to FIG. 4H, in accordance with one embodiment, an outline 180 of test sensor 200 is shown, although any desired shape of test sensor can be obtained. A laser may be used to cut the outline 180 (shown as a thick solid line) of the test sensor. Outline 180 intersects with first edge 128A of opening 128 and first edge 115 of opening 117 of lid 108 to define the shape of the test sensor 200 of FIG. 3. In one embodiment, outline 180 is the only cut necessary to release the sensor from the surrounding material. Providing two separate openings—a first opening 128 in base 102-spacer 104 laminate and a second opening 117 in lid 108—allows at least two lines to cross (i.e., outline 180 of lid 108 and edge 128A of opening 128). This configuration generates the sharp point P (FIG. 3) needed to puncture the burst foil of a blister package which may house a test sensor. It also allows freedom to optimize shapes of the first edge 102A of base 102 and edge 104A of spacer 104 and edge 115 of opening 177 of lid 108. This configuration can also avoid any additional laser cutting that may contribute to more smoke contamination.

During manufacture, the laser will cut through lid 108, spacer 104 and base 102, as necessary to achieve the shape of test sensor 200 shown in FIG. 3. Alternative methods may be used to excise test sensor 200. For example, a mechanical punch or steel-rule die cutting may be used to excise the test sensor. It is to be appreciated that similar method steps may be used to manufacture the test sensor of FIG. 1. The only difference being that the trigger electrode of FIG. 1 will be a pre-determined shape that is patterned from the conductive layer prior to deposition of the protective layer and reactive layer.

It is to be appreciated that the presently disclosed embodiments provide only a few examples of configurations in which a protective layer is used to overlie a trigger electrode. However, there are other numerous components that can be incorporated into the present embodiments. Examples of components of electrochemical test sensors, including their operation, may be found at, for example, U.S. Pat. No. 6,531,040, the disclosure of which is incorporated herein by reference. It is contemplated that other components of electrochemical test sensors may be used other than that disclosed in, for example, U.S. Pat. No. 6,531,040.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as detailed by the following claims.

The invention claimed is:

1. An electrochemical test sensor for detecting the concentration of an analyte in a fluid sample, the test sensor comprising:
   a non-conductive base having a top surface, a bottom surface, and a peripheral edge extending between the top and bottom surfaces;
   a trigger electrode, a working electrode, and a counter electrode overlying the non-conductive base, the trigger electrode adjacent the peripheral edge of the base;
   a protective layer overlying at least a portion of the trigger electrode;
   a reactive layer on at least a portion of the working electrode, the reactive layer including an enzyme for reacting with the analyte to produce electrons which are transferred to the working electrode, wherein the protective layer and the reactive layer are spaced a sufficient distance from each other so that they do not contact each other; and
   a lid overlying the base, the lid having a top surface, a bottom surface, and an outer edge extending between the top and bottom surfaces, the outer edge extending beyond the peripheral edge of the base.

2. The test sensor of claim 1, wherein the protective layer is soluble upon contact with the fluid sample.

3. The test sensor of claim 1, wherein the protective layer is comprised of a polymer solution.

4. The test sensor of claim 3, wherein the polymer solution is carboxymethyl cellulose or hydroxyethyl cellulose.

5. The test sensor of claim 3, wherein the polymer solution has a concentration ranging between 0.25% to 1.0%.

6. The test sensor of claim 5, wherein the concentration of the polymer solution is 0.25%.

7. The test sensor of claim 5, wherein the concentration of the polymer solution is 1.0%.

8. The test sensor of claim 5, wherein the protective layer further comprises a surfactant or rheological additive for increased wettability or processability.

9. The test sensor of claim 1, wherein:
   the base is laminated, printed, coated or sputtered with a conductive layer; and
   each of the trigger, working, and counter electrodes is patterned from the conductive layer.

10. The test sensor of claim 9, wherein the conductive layer is comprised of a metallic material.

11. The test sensor of claim 9, wherein the conductive layer is comprised of a carbon or graphite.

12. The test sensor of claim 1, further comprising a spacer positioned between the base and the lid.

13. The test sensor of claim 12, wherein the spacer includes a spacer channel extending through a portion of the spacer, wherein the spacer is positioned over the base such that the spacer channel overlies each of the trigger, working, and counter electrodes and the protective and reactive layers.

14. An electrochemical test sensor for detecting the concentration of an analyte in a fluid sample, the test sensor comprising:
   a base including a plurality of electrodes formed thereon, the plurality of electrodes including:
      a working electrode having a reactive layer deposited on at least a portion of the working electrode;
      a counter electrode; and
      a reagent-free trigger electrode, wherein the trigger electrode is positioned adjacent an outermost edge of the base and includes a protective layer deposited on at least a portion of the trigger electrode, wherein the protective layer and the reactive layer are spaced sufficiently apart from one another so that they do not contact one another; and
   a lid overlying the base, wherein an outermost edge of the lid extends beyond the outermost edge of the base.

15. A method of manufacturing an electrochemical test sensor for detecting the concentration of an analyte in a fluid sample, the method comprising:
   patterning a plurality of electrodes from a conductive layer overlying a base, the plurality of electrodes including at least a trigger electrode, a working electrode, and a counter electrode;
   depositing a protective layer overlying the trigger electrode;
   depositing a reactive layer overlying the working electrode, wherein the protective layer and the reactive layer are deposited a sufficient distance from one another so that they do not contact one another;
   positioning a spacer over the base;
   creating a first opening extending through the spacer and the base;
   creating a second opening in a lid;
   positioning the lid over the spacer; and
   excising a test sensor.

16. The method of claim 15, wherein the first opening has an inner peripheral edge and the second opening has an inner peripheral edge, wherein the step of positioning the lid over the spacer includes positioning the lid such that at least a portion of an inner peripheral edge of the second opening extends beyond an inner peripheral edge of the first opening so as to define an overhang portion.

17. The method of claim 15, wherein the step of depositing the protective layer includes depositing a polymer layer.

18. The method of claim 17, wherein the step of depositing a polymer layer comprises depositing a layer of carboxymethyl cellulose or hydroxyethyl cellulose.

19. The method of claim 15, wherein the step of patterning comprises ablating through at least a portion of the conductive layer with a laser so as to form an electrode pattern.

20. The method of claim 15, wherein the conductive layer overlying the base is comprised of at least one of gold, platinum, palladium, iridium, rhodium, and ruthenium.

21. The method of claim 15, wherein at least one of the steps of creating the first opening and creating the second opening comprises laser cutting the opening.

22. The method of claim 15, wherein the base is comprised of a flexible insulating substrate.

23. The method of claim 15, wherein the spacer includes a spacer channel extending through a portion of the spacer, and wherein the step of positioning the spacer over the base includes arranging the spacer relative to the base such that the spacer channel overlies each of the trigger, working, and counter electrodes and the protective and reactive layers.

24. The method of claim 23, wherein the step of positioning the lid over the spacer includes arranging the lid relative to the spacer such that the second opening of the lid overlies the spacer channel and an inner peripheral edge of the second opening extends beyond an edge of the trigger electrode.

25. The method of claim 15, wherein the protective layer comprises a polymer solution, and wherein the step of depositing the protective layer comprises using a drop placement technique to deposit at least one droplet of polymer solution on the trigger electrode.

* * * * *

UNITED STATES PATENT AND TRADEMARK OFFICE
CERTIFICATE OF CORRECTION

| | | |
|---|---|---|
| PATENT NO. | : 9,097,659 B2 | Page 1 of 1 |
| APPLICATION NO. | : 13/829447 | |
| DATED | : August 4, 2015 | |
| INVENTOR(S) | : Andrew Edelbrock and Steven C. Charlton | |

It is certified that error appears in the above-identified patent and that said Letters Patent is hereby corrected as shown below:

Title page (72), under "Inventors", in Column 1, Line 1, delete "Andy Edelbrock," and insert -- Andrew Edelbrock, --, therefor.

Signed and Sealed this
Twenty-third Day of February, 2016

Michelle K. Lee
*Director of the United States Patent and Trademark Office*